(12) United States Patent
Casavant et al.

(10) Patent No.: US 7,027,876 B2
(45) Date of Patent: Apr. 11, 2006

(54) LEAD SYSTEM FOR PROVIDING ELECTRICAL STIMULATION TO THE BUNDLE OF HIS

(75) Inventors: David A. Casavant, Reading, MA (US); Douglas N. Hess, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 420 days.

(21) Appl. No.: 10/261,313

(22) Filed: Sep. 30, 2002

(65) Prior Publication Data

US 2003/0083727 A1    May 1, 2003

Related U.S. Application Data

(60) Provisional application No. 60/329,172, filed on Oct. 12, 2001.

(51) Int. Cl.
    *A61N 1/05* (2006.01)

(52) U.S. Cl. .................. 607/126; 607/127; 607/128

(58) Field of Classification Search ................ 607/119, 607/122, 123, 126–127
See application file for complete search history.

(56) References Cited

U.S. PATENT DOCUMENTS

| | | | |
|---|---|---|---|
| 3,472,234 A | 10/1969 | Tachick | 128/418 |
| 4,000,745 A | 1/1977 | Goldberg | 128/418 |
| 4,106,512 A * | 8/1978 | Bisping | 607/127 |
| 4,146,036 A | 3/1979 | Dutcher et al. | 128/418 |
| 4,166,469 A * | 9/1979 | Littleford | 607/122 |
| 4,217,913 A | 8/1980 | Dutcher | 128/785 |
| 4,570,642 A | 2/1986 | Kane et al. | 128/785 |
| 4,762,136 A | 8/1988 | Baker, Jr. | 607/13 |
| 5,076,285 A | 12/1991 | Hess et al. | 128/186 |
| 5,246,014 A | 9/1993 | Williams et al. | 607/122 |
| 6,269,272 B1 | 7/2001 | Fischer, Sr. | 607/127 |
| 6,296,630 B1 * | 10/2001 | Altman et al. | 604/508 |
| 6,609,027 B1 * | 8/2003 | Kroll et al. | 607/9 |

FOREIGN PATENT DOCUMENTS

| | | |
|---|---|---|
| DE | 25 33 766 A1 | 2/1977 |
| DE | 25 39 553 A1 | 3/1977 |
| WO | WO 87/04081 * | 7/1987 |

* cited by examiner

*Primary Examiner*—Carl Layno
(74) *Attorney, Agent, or Firm*—Daniel G. Chapik; Girma Wolde-Michael

(57) ABSTRACT

Methods and endocardial screw-in leads for enabling provision of electrical stimulation to the heart, particularly the His Bundle in the intraventricular septal wall. An endocardial screw-in lead having a distal end coupled to a retractable fixation helix wherein a distal portion of the fixation helix extends beyond the lead distal end when the fixation helix is fully retracted or partially extended is positioned in proximity to the His Bundle in the septal wall. The lead body is rotated to attach the distal portion of the fixation helix into the septal wall. The fixation helix is rotated with respect to the lead body to fully extend the fixation helix so that a portion of the fixation helix is in proximity to the His Bundle, enabling provision of electrical stimulation to the His Bundle and/or to sense electrical signals of the heart traversing the His Bundle through the fixation helix.

22 Claims, 4 Drawing Sheets

LEAD SYSTEM FOR PROVIDING ELECTRICAL STIMULATION TO THE BUNDLE OF HIS

This application claims the benefit of U.S. Provisional Application(s) Ser. No. 60/329,172 filed Oct. 12, 2001.

FIELD OF THE INVENTION

This invention relates to medical electrical leads generally; and, more particularly, to endocardial screw-in pacing leads for pacing the Bundle of His or His Bundle.

BACKGROUND OF THE INVENTION

In an effort to assure the stable location of an endocardial pacing electrode, a variety of approaches have been employed. One approach in common use today is to employ an endocardial pacing lead that has a sharpened tip, active fixation helix located at its distal end. The active fixation helix may either be a pacing electrode or may be located adjacent the pacing electrode(s) of unipolar, bipolar and multi-polar leads. Typically, the active fixation helix is rotated by some means from the proximal end of the lead and screwed through the endocardium into the myocardium to permanently fix the electrode in operative relation to cardiac tissue. A number of different varieties of endocardial screw-in pacing and cardioversion/defibrillation leads have been clinically used or proposed for use over the years.

Current endocardial screw-in leads have evolved from early epicardial and endocardial screw-in lead designs that employed wire coils or fixation helixes that were fixedly mounted to extend distally from the lead body distal end in axial alignment with the lead body axis. Epicardial screw-in leads were proposed for affixation of the sharpened fixation helix into the myocardium at a site exposed through a surgical exposure prior to endocardial screw-in leads. Such epicardial screw-in leads are exemplified by those disclosed in U.S. Pat. Nos. 3,472,234 to Tachick et al. and 4,000,745 to Goldberg. Later, endocardial screw-in leads, exemplified by those disclosed in U.S. Pat. No. 4,146,036 to Dutcher et al. and in German Patent No. 2533766, 2539553, issued to Osypka, were developed and clinically used. In these early epicardial and endocardial screw-in leads, rotation of the fixation helix into the heart tissue is accomplished either by rotation of the entire lead, or by rotation of a stylet with a screwdriver tip that engages a slot located internal to the pacing lead distal end or the fixation helix itself.

The exposed sharp tip of the fixation helix makes it difficult to advance the fixation helix transvenously from a skin incision into the right atrium and through the tricuspid valve or the coronary sinus ostium if the electrode(s) is to be fixed in the right ventricle or the coronary sinus or branching coronary vessel. Thus, many endocardial screw-in lead designs have been disclosed that employ fixation helixes that housed within a housing or protective sheath at the lead body distal end during advancement of the pacing lead through the venous system and the tricuspid valve without the possible danger of tissue damage caused by the extended fixation helix distal tip. A mechanism is provided to then extend the fixation helix distally from the housing or sheath so that it may be screwed into the heart tissue. An early version of such a retractable screw-in lead is illustrated in U.S. Pat. No. 4,106,512 issued to Bisping. In this example, the fixation helix is attached to the distal end of the coiled wire conductor extending proximally to the lead connector assembly and functions as an electrode. The fixation helix is advanced out of the housing the lead body distal end by rotation of the coiled wire conductor within a lead body lumen.

An alternative approach is illustrated in U.S. Pat. No. 4,217,913, issued to Dutcher wherein the fixation helix is mounted for rotation out of the distal housing. A screwdriver tip stylet is extended through a stylet lumen into engagement with a shaped receptacle of the fixation helix mounting and rotated at the stylet proximal end to rotate the fixation helix out of the lead body distal end. In this case, the fixation helix serves only to attach the lead body distal end to heart tissue, and a separate ring electrode(s) is mounted to the lead body and coupled to the lead conductor(s) for pacing and sensing.

Yet another approach is illustrated in U.S. Pat. No. 4,570,642 issued to Kane et al. wherein the fixation helix is located on a member that is slidable within a receptacle at the lead body distal end. The fixation helix is advanced from a lead body distal end housing by insertion of a cylindrical stylet through the stylet lumen into engagement with the slidable member to push the fixation helix distally and out of the housing. The fixation helix is then screwed into the tissue by rotation of the entire lead from the lead body proximal end.

The above-cited patents illustrate alternative approaches for attaching a fixation helix to cardiac tissue within the atrial or ventricular chambers of the heart. These types of approaches are generally best suited for placement within the ventricular apex or the atrial appendage. However, studies have indicated this may not be the most desirable location to provide electrical stimulation for pacing applications.

In a normal heart, a contraction results from the spontaneous excitation of the sinus node cells located in the upper right atrium. The electrical activity spreads throughout the atrium and eventually reaches the atrio-ventricular (AV) node. After passing through the AV node, the activity proceeds through nerve fibers called the His Bundle to the right and left bundle branches. From the bundle branches, the signal propagates through many parallel exits to the ventricular myocardium. The resulting depolarization wave spreads through the muscular tissue of the ventricle to cause the ventricle to contract, producing the ventricle pumping action.

As may be apparent from the above discussion, providing pacing and sensing at the apex of the right ventricle bypasses some of the body's normal conduction mechanism. That is, the conduction pathways of the His Bundle and right and left bundle branches are not utilized to sense natural heart depolarizations and to conduct a pace-triggered depolarization. As a result, conduction within the right and left ventricles may not be optimally synchronized. A more effective form of stimulation may involve pacing the His Bundle, which improves the synchronization between contractions in the left and right cardiac chambers.

Currently available endocardial screw-in leads have fixation helixes that are relatively short to avoid perforation through the heart wall when the fixation helix is rotated. For example, the MEDTRONIC® Model 5076 extendable-retractable endocardial screw-in lead, has a distal fixation helix that is about 1.8 mm in axial length. The fixation helix is coupled to the lead conductor and retractable and extendable from a distal housing through rotation of a torque tool applied to the lead connector assembly that rotates the lead conductor with respect to the lead body. The fixation helix tip is fully retracted into the lead body distal end housing during transvenous advancement through the vascular system and the tricuspid valve, when the fixation helix is to be screwed into the right ventricular wall. Due to frictional losses of torque, in many cases, it is necessary to rotate the torque tool through more turns than the fixation helix turns to ensure that the distal fixation helix is rotated through its number of turns. But, the physician cannot observe the number of turns that the fixation helix makes, and over-rotation can occur. This is one reason why the number of turns and the axial length of the fixation helix are limited.

It has been proposed to affix endocardial screw-in fixation helixes along the septal wall separating the right and left atrium as shown, for example, in U.S. Pat. No. 5,246,014 to Williams et al. However, prior art fixation helixes and other fixation mechanisms are not particularly adapted for pacing the His Bundle. This is because prior art fixation mechanisms are generally not long enough to penetrate the His Bundle and directly stimulate it to capture the cardiac tissue. What is needed, therefore, is a fixation mechanism that is adapted for fixation in proximity to the His Bundle.

SUMMARY OF THE INVENTION

According to one aspect of the invention, a lead for providing electrical stimulation to a His Bundle of a heart is described. The lead includes a lead body, a conductor residing within the lead body, and a fixation mechanism coupled to the conductor distal end. The fixation mechanism has a length selected to allow a distal end of the fixation mechanism to be proximal to the Bundle of His when the fixation mechanism is affixed to tissue surrounding the Bundle of His. The fixation mechanism is preferably between 2.5 and 7 millimeters in length.

According to yet another aspect of the invention, an electrode system is provided for electrically stimulating the His Bundle of a heart. The electrode system includes a housing member, and a fixation member such as a fixation helix positioned within the housing member. The fixation member is sized to penetrate tissue of the heart to contact the His Bundle. The fixation member may be fully retractable within the lead body. Alternatively, a portion of the fixation member may extend beyond a distal end of the lead body when it is in its fully retracted position.

In another embodiment, the invention includes methods for providing electrical sensing and stimulation to a heart via an endocardial screw-in lead having a distal end coupled to a retractable fixation helix functioning as an electrode, wherein a distal portion of the fixation helix extends beyond the lead distal end when the fixation helix is fully retracted or partially extended. The method includes the steps of positioning the lead in proximity to the His Bundle in the heart, rotating the lead body to attach the distal portion of the fixation helix to tissue of the heart, then rotating the fixation helix with respect to the lead body to fully extend the fixation helix so that a portion of the fixation helix is in proximity to the His Bundle to enable provision of electrical stimulation, e.g., pacing pulses, to the His Bundle and/or to sense electrical signals of the heart traversing the His Bundle through the fixation helix.

Other aspects of the invention will become apparent from the drawings and the accompanying description.

DETAILED DESCRIPTION OF THE DRAWINGS

The current invention relates to an improved lead and lead fixation mechanism for pacing the His Bundle.

Figure 1:
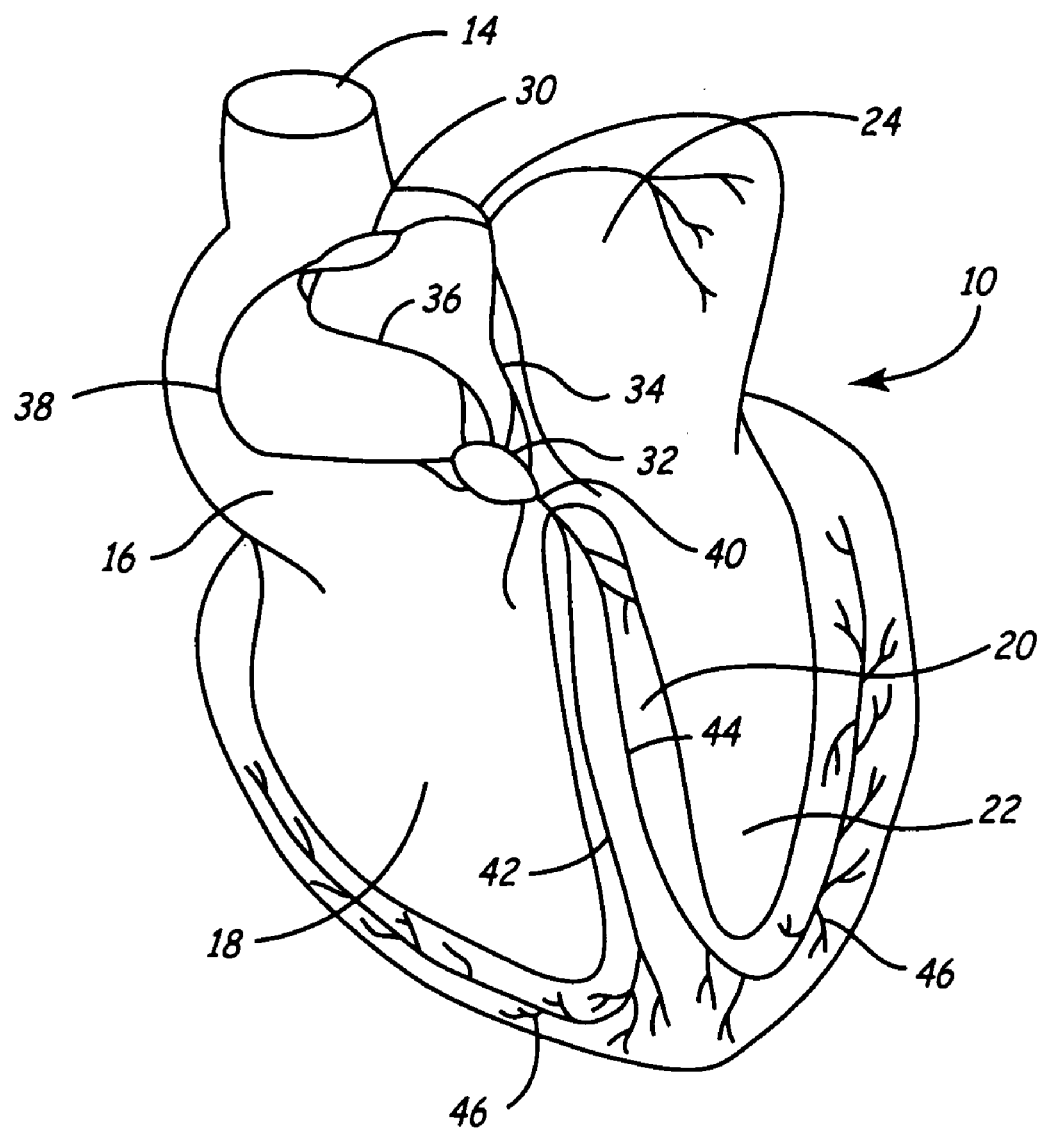
FIG. 1 a diagram of a human heart.

FIG. 1 is a diagram of a human heart. The heart includes right and left atria 16 and 24, respectively, and right and left ventricles 18 and 22, respectively, separated by the ventricular septum 20. The sino-atrial (S-A) node 30 is embedded within muscular tissue in the wall of the right atrium 16 around the opening of the superior vena cava 14. The S-A node is connected to the atrio-ventricular (A-V) node 32 by means of conductive pathways including a posterior internodal tract 34, a mid-internodal tract 36, and an anterior internodal tract 38. The A-V node 32 transmits the impulses to a nerve group known as the His Bundle 40, which is situated below the medial leaflet of the tricuspid valve. From there, the signal is transferred to the right bundle 42 and the left bundle 44. The right bundle 42 is made of a long, thin fascicle that runs along the ventricular septum 20 to branch out into the Purkinje fibers of the right ventricle. The left bundle 44 is formed by a long thin anterior fascicle and a shorter posterior fascicle that both extend into the left ventricular Purkinje fibers. The Purkinje fibers 46 propagate the signal within the myocardium of the two ventricles.

Pacing at the His Bundle 40 provides the advantage of utilizing the normal conduction system of the heart to carry out the ventricular depolarizations. In other words, stimulation provided at the His Bundle will travel via the right and left bundles 42 and 44, respectively, and the Purkinje fibers 46 to the apex of the ventricle. This provides more synchronized and efficient ventricular contractions than are provided by pacing at the apex of the right ventricle.

Similarly, sensing the EGM traversing the His Bundle is advantageous in providing accurate timing information to the pacing system and to distinguish abnormal signal propagation from normal signal propagation.

Pacing and sensing at the His Bundle 40 requires a specialized electrode because the nerve fibers associated with the His Bundle are embedded within the heart muscle tissue. To provide stimulation to these fibers, an electrode that can penetrate the tissue at a greater depth is required. A longer fixation helix may be used for this purpose, but longer fixation helixes are difficult to manipulate to the site of interest.

Secondly, it is desirable to be able to ascertain optimal implantation sites of the ventricular septum to implant the pace/sense electrode, which, in this case advantageously would comprise at least the portion of the fixation helix closest to the His Bundle. The endocardial screw-in lead delivery system of the present invention enables mapping of the His Bundle before the fixation is completed to determine the optimum site of implantation.

Figure 2:
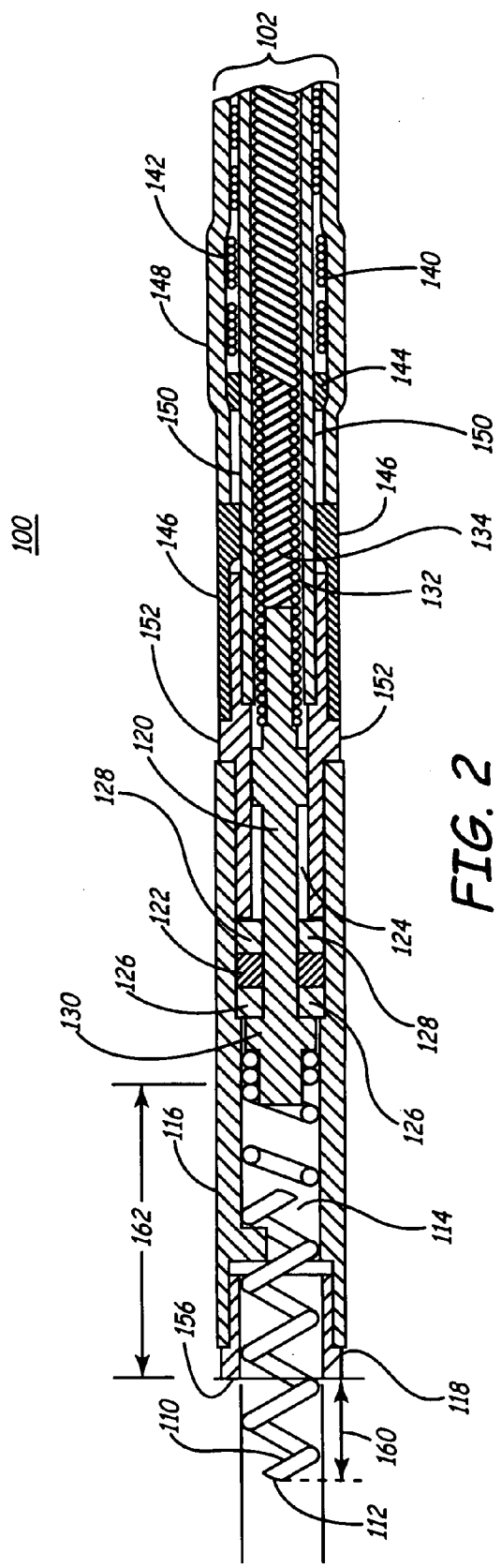
FIG. 2 is a side, cut away view of the distal end of a pacing lead according to one embodiment of the present invention.

FIG. 2 is a side, cut away view through the distal end of an endocardial screw-in lead 100 according to one embodiment of the present invention comprising a lead body 102 extending between a lead body proximal end (not shown) and a lead body distal end 156 and having the distal fixation helix 110 in axial alignment with the lead body axis.

FIG. 2 illustrates fixation helix 110 retracted to its fully retracted position where the distal tip 112 is exposed from the electrode housing or chamber 114. A distal portion 160 of fixation helix 110 extends distal to the lead body distal end 156 to the sharpened, distal tip 112, and a proximal portion 162 of fixation helix 110 is contained within an electrode chamber 114 defined by sleeve head 116. Fixation helix 110 is preferably constructed of an inert, biocompatible metal such as MP35N alloy, Elgiloy alloy, or a platinum alloy. Preferably the proximal portion 162 of fixation helix 110 is covered by an insulating tube or coating in a manner well known in the art so that the distal portion 160 and sharpened helix tip 112 are exposed and function as pace/sense electrodes when screwed deeply into the septum in relation to the His Bundle. In this illustrated embodiment, fixation helix 110 has a generally constant diameter, although in other embodiments, it may be a conical, tapered fixation helix as illustrated in commonly assigned U.S. Pat. No. 5,076,285 incorporated herein by reference.

Sleeve head 116 may be fabricated of polyurethane, silicone rubber, or any other type of suitable biocompatible polymer. Sleeve head 116 may be further coupled to a Monolithic Controlled Release Device (MCRD) 118 impregnated with a glucocorticosteroid or another steroid to counter thrombus formation, fibrosis, inflammation or arrhythmias, or to accomplish any other localized purpose. The MCRD 118 may be coupled to sleeve head 116 using a medical grade adhesive.

Fixation helix 110 is electrically and mechanically coupled as via a spot weld or other suitable mechanism to drive shaft 120. Drive shaft, which may be formed of any biocompatible conductive material, is seated within a sealing ring 122, which is provided to prevent fluid ingress into an inner lumen 124 of the lead. Fluorovisible "C" indicators 126 and 128 may further be provided to determine when the fixation helix is in a fully retracted position. When the fixation helix 110 is fully retracted as shown in FIG. 2, the stop member 130 of drive shaft 120 closes a gap existing between indicators 126 and 128. The closing of this gap may be viewed using a fluoroscope to determine that the fixation helix is in a fully retracted state.

Drive shaft 120 may be electrically and mechanically coupled to an internal coiled wire conductor 132 via a weld, a crimping sleeve or other type of suitable coupling mechanism. Coiled wire conductor 132, which may be formed of any of the known biocompatible conductive materials used to form lead conductors, is in a fixed rotational relationship to the fixation helix 110. This allows for the transfer of torque to fixation helix 110 via rotation imparted through the connector assembly coupled with the proximal end of coiled wire conductor 132.

Coiled wire conductor 132 defines an internal stylet lumen 134 adapted to receive a stylet (not shown). In a variation of the embodiments of the invention, the proximal end of drive shaft 120 may include a slot to receive a keyed distal end of a stylet introduced through the stylet lumen 134. The stylet may be used to facilitate lead placement as discussed further below.

Coiled wire conductor 132 is shown residing within an elongated insulative sheath 140. Sheath 140 is preferably made of an implantable polymer such as silicone rubber or polyurethane. In the illustrated bipolar embodiment, sheath 140 extends to the proximal end of the lead to insulate coiled wire conductor 132 from a second coiled wire conductor 142. The second coiled wire conductor 142 is electrically and mechanically coupled to the proximal end 144 of a ring electrode 146 as via a weld. In a unipolar lead embodiment, sheath 140, second coiled wire conductor 142, and ring electrode 146 may be eliminated.

An insulating lead sheath 148 that extends from the MCRD 118 to the proximal end of the screw-in lead 100 surrounds coiled wire conductor 142. Insulating lead sheath 148 is constructed of a biocompatible polymer such as polyurethane or silicone rubber. The distal end of the insulating lead sheath 148 may be coupled to ring electrode 146 via medical grade adhesive. This adhesive may be infused into pocket areas 150. These pocket areas are accessed via apertures or windows (not shown) provided in ring electrode 146.

The embodiment of FIG. 2 further illustrates a coupler 152 to couple ring electrode 146, as well as the proximal portion of the lead, to sleeve head 116. Coupler 152 is coupled to the electrode 146 and the sleeve head 116 via medical grade adhesive.

The lead body of the current invention includes a connector assembly at the lead body proximal end (not shown) that may be coupled to any type of standard or non-standard connector adapted to mate with the connector block of an implantable pulse generator or other implantable medical device.

As discussed above, fixation helix 110 is shown in its fully retracted state wherein the distal portion 160 of fixation helix 110 extends beyond the distal end 156 of the lead body 102. In one embodiment, the length of the fixation helix is between 2.5 and 7 millimeters in length. Preferable, the fixation helix is between 3 and 5 millimeters long. In a more specific embodiment, the fixation helix is 3.3 mm in length, with the distal portion 160 being 1.5 mm in length. The fixation helix 110 therefore has an extended length adapted for penetrating to the His Bundle within the septal wall to locate the electrically exposed distal portion 160 in optimal relation therewith for pacing and sensing. A guide catheter is preferably employed during the transvenous advancement of the lead distal end 156 and fixation helix 110 into the right ventricle so that the exposed sharpened tip 112 does not snag and damage tissue and/or cause inhibit advancement.

Figure 4:
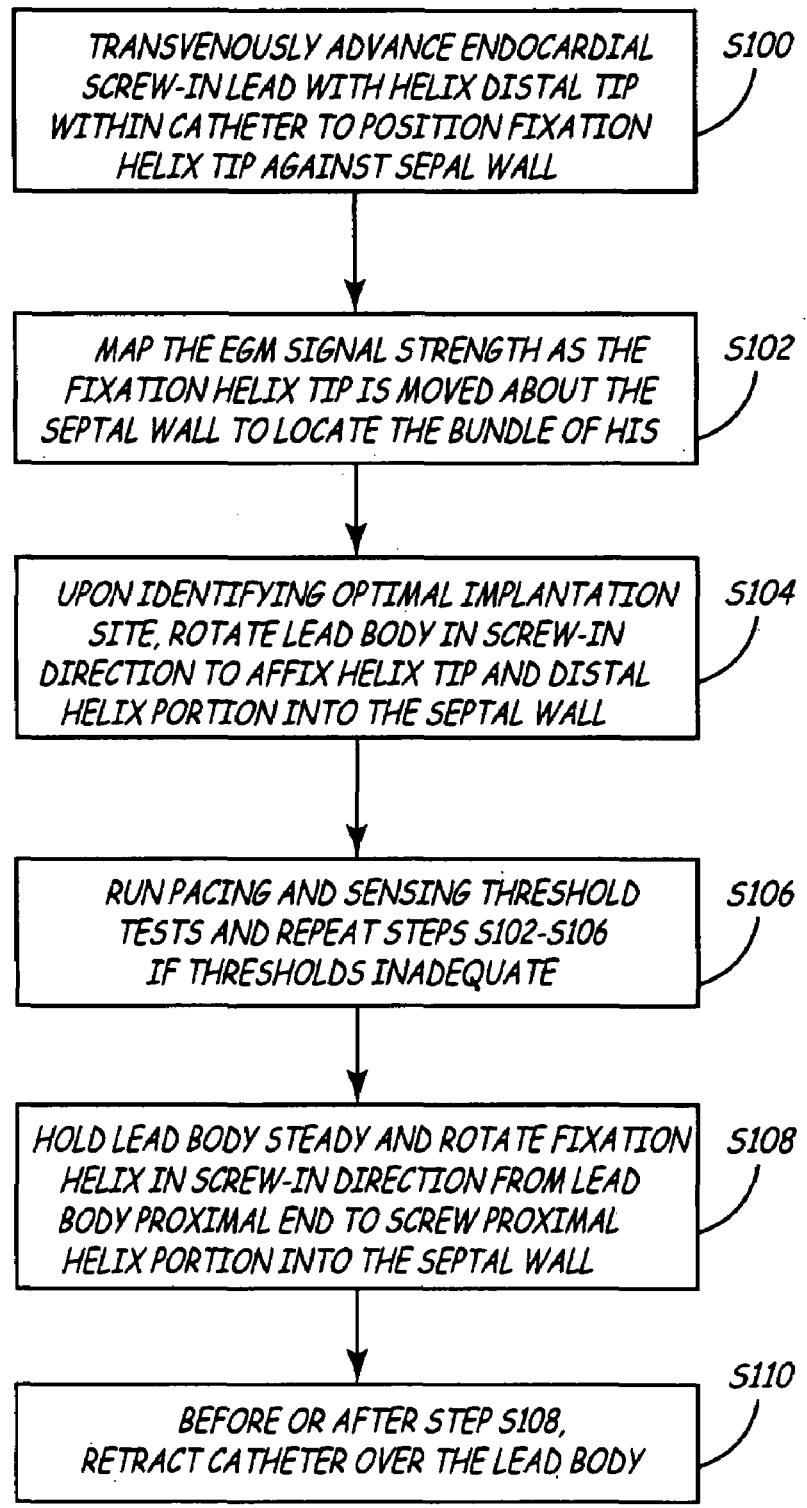
FIG. 4 is a flow diagram illustrating embodiments of providing treatment using the inventive lead system.

FIG. 4 is a flow diagram illustrating one embodiment of providing treatment using the inventive endocardial screw-in lead 100. The endocardial screw-in lead 100 and catheter enclosing the fixation helix distal portion is advanced in step S100 into the right ventricle. The lead body, catheter and optional stylet within the stylet lumen are manipulated to position the exposed distal tip 112 of the fixation helix 110 in proximity to the septal wall that the His Bundle is embedded in. The septal wall can be mapped by moving the distal tip 112 about it to ascertain the strongest signal strength of the EGR traversing the His Bundle in step S102. Once a site is determined, the catheter can be retracted slightly as the entire lead body 102 is rotated in the screw-in direction in step S104. The distal portion 160 extending beyond the lead distal end 156 is then affixed to tissue by rotating the entire lead body 102 from the proximal end thereof. The rotation of the entire lead body 102 provides a robust penetration of the endocardium and initial fixation. Optionally, pacing and sensing threshold measurements can be made in step S106 to be assured that the implantation site is satisfactory.

If the implantation site is satisfactory, then the distal portion 160 of the fixation helix can be advanced more deeply into the septal wall into closer proximity to the His Bundle therein by rotation of the fixation helix 110 while the lead body is held or remains steady in step S108. The efficacy of pacing and sensing at differing depths can be assessed by repeating step S106 at each turn. Step S108 can be accomplished by rotation of the proximal connector assembly in the construction depicted in FIG. 2, or by rotation of a stylet keyed to the fixation helix if the fixation helix is supported for rotation within the chamber by a keyed stylet extended through the lead wire lumen.

The catheter is retracted completely in step S110, either before or after step S108. This may be accomplished by utilizing a low-profile connector on the proximal end of the lead. Alternatively, a splittable or slittable sheath or catheter may be employed.

Figure 3:
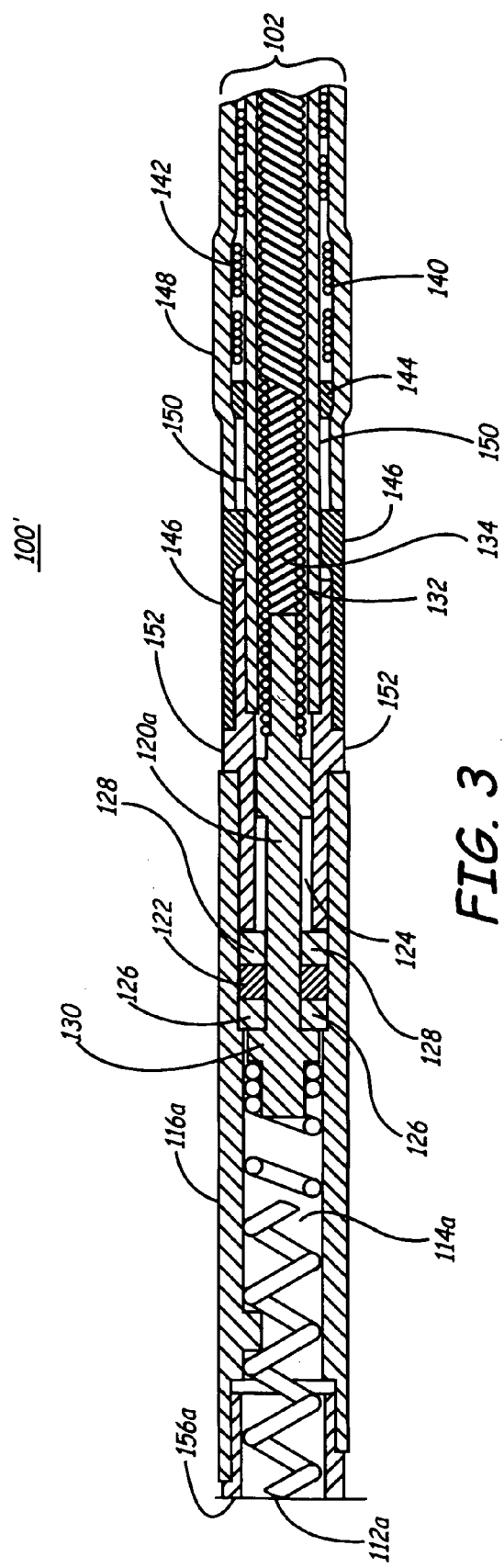
FIG. 3 is a side, cut away view of the distal end of a pacing lead according to alternative embodiment of the present invention.

FIG. 3 illustrates an alternative embodiment of an endocardial screw-in lead 100' of the invention that can be implanted with or without catheter guidance. In this embodiment, the length of the sleeve head 116a is extended to provide an electrode chamber 114a that is long enough to receive the entire length of the fixation helix 110a when the fixation helix 110a is fully retracted as shown in FIG. 3. In this embodiment, the fixation helix 110a may be positioned such that the distal end 156a of the lead body is substantially flush with the helix distal end 112a during the advancing step S100 of FIG. 4. In this manner, the fixation helix distal end 112a may be used for mapping in step S102 during the lead placement operation when the fixation helix 110a is in the fully retracted state.

The endocardial screw-in lead 100' depicted in FIG. 3 provides the advance of guarding the fixation helix distal tip 112a from tissue during the lead placement operation without use of a guide catheter. The retraction prevents inadvertent tissue damage from occurring as the lead is guided through the venous system and heart chambers. However, this alternative embodiment may be undesirable because of the added dimensions associated with sleeve head 116a and drive shaft 120a, which, in turn, impose slightly different handling characteristics in directing the distal lead end to a desired site of fixation of the fixation helix 11a.

When a site is determined as in step S102, a distal portion of the fixation helix 110a can be exposed by rotation of the lead conductor 132 via the lead connector assembly as described above through a limited number of turns. Then, the lead body can be rotated to screw the distal portion into the septal wall, and steps S106 and S108 can be followed to complete the implantation.

As noted above, the inventive leads 100 and 100' may be catheter delivered, or may be delivered using a stylet inserted within internal lumen 134 of coiled wire conductor 132. Any of the many types of stylets and guide catheters known in the art may be adapted for this purpose, including a stylet having a curvature imposed on the stylet distal end. Alternatively, both a stylet and catheter may be used in conjunction when placing the lead. For example, a guide catheter may be utilized to locate the lead in a general vicinity of the His Bundle. A stylet may then be inserted into lumen 134 to accomplish precise placement of the fixation helix tip.

A similar delivery method may be utilized to deliver the alternative embodiment shown in FIG. 3. In this instance, however, fixation helix extension may be accomplished solely through rotation of coiled wire conductor 132 from the lead connector assembly.

In both embodiments, it may desirable to screw the fixation helix 110, 110a in only enough so that the exposed electrode surface is closest to the His Bundle such that the fixation helix remains in a partially retracted state during chronic pacing. Such a location may be beneficial to prevent unnecessary damage to the tissue. The amount of fixation helix extension required to contact the His Bundle may vary based on the particular physiology of a patient. To determine the amount of extension required to make adequate contact and capture the heart, a clinician may monitor signals received by the lead as the fixation helix is extended. Alternatively, the clinician may deliver pacing pulses to determine whether adequate capture is achieved. Such determinations will allow the physician to determine whether the fixation helix is in contact with the His Bundle, indicating the extension is adequate.

According to the current invention, an increased surface area provided by the extended fixation helix length may be contact with cardiac tissue. This increased surface reduces the electrical impedance of the electrode, thereby decreasing the effectiveness of the pacing stimulation. To achieve capture, the pacing threshold may therefore have to be increased, resulting in a shortened battery life. To increase impedance, a portion of the fixation helix surface may be coated or covered with a biocompatible electrical insulator such as silicone, polyurethane, an enamel, glass, or any other insulator known in the art.

Other aspects and embodiments of the current lead and fixation system are possible within the scope of the present invention, which is therefore to be defined by the following claims.

What is claimed is:

1. A lead for providing electrical stimulation to a His Bundle of a heart, comprising:
   a lead body having a distal end;
   a conductor residing within the lead body and having a distal end;
   a fixation mechanism coupled to the conductor distal end, the fixation mechanism having a length selected to allow a distal end of the fixation mechanism to be proximal to the Bundle of His when the fixation mechanism is affixed to tissue surrounding the Bundle of His, wherein a distal end of the fixation mechanism extends beyond the distal end of the lead body when the fixation mechanism is fully retracted.

2. The lead system of claim 1, wherein the fixation mechanism is a fixation helix.

3. The lead system of claim 2, wherein the fixation helix is substantially between 2.5 and 7 millimeters in length.

4. The lead system of claim 2, wherein the fixation helix is substantially between 3 and 5 millimeters in length.

5. The lead of claim 3, wherein substantially the entire length of the fixation helix resides within the lead body when the fixation helix is in a fully retracted state.

6. The lead of claim 1, and further comprising:
   a second conductor residing within the lead body; and
   a ring electrode coupled to the second conductor.

7. An electrode system for providing electrical stimulation to a His Bundle of a heart, comprising:
   a housing member;
   a fixation member positioned within the housing member, the fixation member being sized to penetrate tissue of the heart to contact the His Bundle, wherein the fixation member is a fixation helix a distal end of the fixation helix extends beyond the housing member when the fixation helix is fully retracted.

8. The electrode system of claim 7, wherein the fixation helix is substantially between 2.5 and 7 millimeters in length.

9. The electrode system of claim 7, wherein the fixation helix is substantially between 3 and 5 millimeters in length.

10. The electrode system of claim 7, wherein substantially the entire length of the fixation helix resides within the housing member when the fixation helix is in a fully retracted state.

11. A method for enabling provision of electrical stimulation to a heart and sensing of heart signals via a endocardial screw-in lead having a lead body distal end supporting an extendable and retractable fixation helix operable as a stimulation and sensing electrode, the method comprising:

advancing the catheter and lead into a ventricular heart chamber;

positioning the lead body distal end in proximity to the His Bundle in the septal wall of the ventricle;

rotating the lead body to attach the distal portion of the fixation helix into the septal wall of the heart;

rotating the fixation helix with respect to the lead body to extend the fixation helix into the septal wall to dispose the fixation helix in proximity to the His Bundle to enable provision of electrical sensing and stimulation through the fixation helix to the His Bundle, further comprising the step of performing pacing and sensing threshold tests following attachment of the distal portion of the fixation helix.

12. The method of claim 11, wherein the positioning step further comprises mapping the septal wall employing the distal fixation helix to ascertain the His Bundle location.

13. A method for enabling provision of electrical stimulation to a heart via an endocardial screw-in lead having a lead body distal end supporting an extendable and retractable fixation helix operable as a sensing and stimulation electrode, a distal portion of the fixation helix extending distally beyond the lead body distal end when a proximal portion of the fixation helix is fully retracted into a chamber of the lead body, the method comprising:

inserting the lead through a catheter lumen to dispose the distal portion of the fixation helix within the catheter lumen;

advancing the catheter and lead into a ventricular heart chamber;

positioning the lead body distal end in proximity to the His Bundle in the septal wall of the ventricle;

rotating the lead body to attach the distal portion of the fixation helix into the septal wall of the heart;

rotating the fixation helix with respect to the lead body to extend the proximal portion of the fixation helix into the septal wall to dispose the fixation helix in proximity to the His Bundle to enable provision of electrical sensing and stimulation through the fixation helix to the His Bundle, further comprising the step of performing pacing and sensing threshold tests following attachment of the distal portion of the fixation helix.

14. The method of claim 13, wherein the positioning step further comprises mapping the septal wall employing the distal fixation helix to ascertain the His Bundle location.

15. A method for enabling provision of electrical stimulation to a heart and sensing of heart signals via a endocardial screw-in lead having a lead body distal end supporting an extendable and retractable fixation helix operable as a stimulation and sensing electrode, the method comprising:

advancing the catheter and lead into a ventricular heart chamber;

positioning the lead body distal end in proximity to the His Bundle in the septal wall of the ventricle;

rotating the fixation helix with respect to the lead body to extend a distal portion of the fixation helix from the lead body distal end;

rotating the lead body to attach the distal portion of the fixation helix into the septal wall of the heart;

rotating the fixation helix with respect to the lead body to extend a proximal portion of the fixation helix into the septal wall to dispose the fixation helix in proximity to the His Bundle to enable provision of electrical stimulation and sensing through the fixation helix to the His Bundle; and performing pacing and sensing threshold tests following attachment of the distal portion of the fixation helix.

16. The method of claim 15, wherein the positioning step further comprises mapping the septal wall employing the distal fixation helix to ascertain the His Bundle location.

17. A lead for providing electrical stimulation to a His Bundle of a heart, comprising:

a lead body having a distal end;

a conductor residing within the lead body and having a distal end;

an extendable fixation mechanism coupled to the conductor distal end and extendable from a retracted position to an extended position, wherein a portion of the fixation mechanism extends distal from the lead body and rotational movement between the fixation mechanism and the lead body is precluded when the fixation mechanism is in the retracted position.

18. The lead of claim 17, wherein the fixation mechanism is a fixation helix.

19. The lead of claim 18, wherein the fixation helix is substantially between 2.5 and 7 millimeters in length.

20. The lead of claim 18, wherein the fixation helix is substantially between 3 and 5 millimeters in length.

21. The lead of claim 17, and further comprising:

a second conductor residing within the lead body; and a ring electrode coupled to the second conductor.

22. An electrode system for providing electrical stimulation to a His Bundle of a heart, comprising:

a housing member;

an extendable fixation member positioned within the housing member and moveable from a retracted position wherein the fixation member is locked with respect to the housing and an extended position wherein the fixation member is rotationally moveable relative to the housing, wherein a portion of the fixation member is exposed distally from the housing member when the fixation member is in the retracted position.

* * * * *